(12) United States Patent
Sun et al.

(10) Patent No.: US 11,768,166 B2
(45) Date of Patent: Sep. 26, 2023

(54) SYSTEM AND METHOD FOR MEASURING VOID FRACTION OF INSIDE OF HEAT CONDUCTION MEMBER

(71) Applicant: NATIONAL TAIWAN UNIVERSITY, Taipei (TW)

(72) Inventors: Chen-Li Sun, Taipei (TW); Yu-Hsiang Liu, Taipei (TW); Yu-Jen Lien, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 57 days.

(21) Appl. No.: 17/529,269

(22) Filed: Nov. 18, 2021

(65) Prior Publication Data

US 2022/0291161 A1    Sep. 15, 2022

(30) Foreign Application Priority Data

Mar. 10, 2021  (TW) .................................. 110108497

(51) Int. Cl.
*G01N 27/22* (2006.01)
*G01K 3/14* (2006.01)
*G01N 33/00* (2006.01)

(52) U.S. Cl.
CPC .............. *G01N 27/22* (2013.01); *G01K 3/14* (2013.01); *G01N 27/228* (2013.01); *F28F 2200/005* (2013.01); *G01N 2033/0078* (2013.01)

(58) Field of Classification Search
CPC ................. G01N 27/22; G01N 27/228; G01N 2033/0078; G01N 27/02; G01N 27/226; G01K 3/14; G01K 1/026; F28F 2200/005
See application file for complete search history.

(56) References Cited

U.S. PATENT DOCUMENTS

| 8,820,175 | B1 * | 9/2014 | Ahmed | ................... G01F 1/688 |
| | | | | 73/861.04 |
| 2009/0196325 | A1 * | 8/2009 | Liu | ........................ G01K 17/00 |
| | | | | 374/147 |
| 2017/0307558 | A1 * | 10/2017 | Chainer | ................... H01L 23/42 |
| 2018/0031330 | A1 | 2/2018 | Roberts et al. | |
| 2018/0303006 | A1 * | 10/2018 | Chainer | ............. H05K 7/20809 |

FOREIGN PATENT DOCUMENTS

| CN | 101680723 A | | 3/2010 |
| JP | 2009210500 A | * | 9/2009 |

* cited by examiner

*Primary Examiner* — Feba Pothen
(74) *Attorney, Agent, or Firm* — Li & Cai Intellectual Property Office

(57) ABSTRACT

A system and a method for measuring a void fraction of an inside of a heat conduction member are provided. The system is used to measure the heat conduction member and includes: a heating device configured as a heat source to heat an evaporation end of the heat conduction member; a cooling device configured for cooling a condensation end of the heat conduction member; at least one pair of electrode pads respectively attached to two opposite surfaces of the heat conduction member; and an LCR meter electrically connected to the at least one pair of the electrode pads for measuring impedances of the heat conduction member. Each of the impedances is converted into the void fraction that corresponds to a measured position of the heat conduction member.

14 Claims, 7 Drawing Sheets

SYSTEM AND METHOD FOR MEASURING VOID FRACTION OF INSIDE OF HEAT CONDUCTION MEMBER

CROSS-REFERENCE TO RELATED PATENT APPLICATION

This application claims the benefit of priority to Taiwan Patent Application No. 110108497, filed on Mar. 10, 2021. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a system and a method for measuring a void fraction of an inside of a heat conduction member, and more particularly to a system and a method for measuring a void fraction of an inside of a vapor chamber or a heat pipe.

BACKGROUND OF THE DISCLOSURE

A vapor chamber and a heat pipe have the same function and working principle. To manufacture the vapor chamber and the heat pipe, a metal housing, a capillary structure, and a working fluid undergo processes of annealing, vacuuming, sealing, etc. The difference between the vapor chamber and the heat pipe resides in that heat conduction of the heat pipe is one-dimensional, and heat conduction of the vapor chamber is two-dimensional. While the working principle of the vapor chamber is similar to that of the heat pipe, the two-dimensional heat conduction of the vapor chamber allows heat energy to spread out rapidly and horizontally. In this way, partial over-heating can be prevented, and outer layers can subsequently achieve good heat dissipation. Hereinafter, the vapor chamber and the heat pipe are collectively referred to as "heat conduction members".

The working principle of the heat conduction member is to have a cyclic process of evaporation and condensation of the working fluid sealed in a chamber and to have the fluid pulled along via the internal capillary structure, so as to achieve excellent and rapid heat conduction.

A heat dissipation performance of the heat conduction member can be affected by an amount of the working fluid inside the heat conduction member, a type of the working fluid, and a hydrophilic property of the capillary structure. Different fill rates of the working fluid can also affect the heat dissipation performance of the heat conduction member. If the fill rate is too large, some of the working fluid can remain at a side surface and a corner of the heat conduction member, causing the fluid inside the chamber to be blocked and difficult to flow. Conversely, if the fill rate is too low, there is a risk of the fluid inside the heat conduction member being dried out. Further, when a heat flux is too high, a dryout condition can also occur in the heat conduction member.

Therefore, a vapor-liquid distribution in the heat pipe and the vapor chamber has a significant influence on a cooling effect thereof. In addition, when the dryout condition occurs, a heat dissipation effect of the heat pipe or the vapor chamber can deteriorate significantly. Since the heat pipe and the vapor chamber are both operated under a sealed state, use of a conventional invasive measurement is not appropriate.

SUMMARY OF THE DISCLOSURE

In response to the above-referenced technical inadequacies, the present disclosure provides a system and a method for measuring a void fraction of an inside of a heat conduction member. By measuring impedances of the heat conduction member, a vapor-liquid distribution in the heat conduction member can be calculated. A safe range of a heat flux of the heat conduction member can be further obtained by measuring the void fraction of the inside of the heat conduction member.

In one aspect, the present disclosure provides a system for measuring a void fraction of an inside of a heat conduction member. The system is used to measure the heat conduction member and includes: a heating device configured as a heat source to heat an evaporation end of the heat conduction member; a cooling device configured for cooling a condensation end of the heat conduction member; at least one pair of electrode pads respectively attached to two opposite surfaces of the heat conduction member; and an LCR meter electrically connected to the at least one pair of the electrode pads for measuring impedances of the heat conduction member. Each of the impedances is converted into the void fraction that corresponds to a measured position of the heat conduction member.

In another aspect, the present disclosure provides a method for measuring a void fraction of an inside of a heat conduction member. The method includes steps as follows: heating an evaporation end of the heat conduction member; cooling a condensation end of the heat conduction member; using at least one pair of electrode pads for measurement of impedances of the heat conduction member; and establishing a relation between an impedance value measured by an LCR meter and the void fraction of the heat conduction member, so as to obtain the void fraction of a measured position of the heat conduction member.

Therefore, in the system and the method for measuring the void fraction of the inside of the heat conduction member provided by the present disclosure, the vapor-liquid distribution in the heat conduction member can be calculated by measuring the impedances thereof, and a conventional invasive measurement can be avoided. Since liquid water and water vapor have different permittivities, and since the permittivity is an important parameter affecting an impedance value, the void fraction of the inside of the heat conduction member can be obtained by measuring the impedance value of the heat conduction member, so that a visualization effect can be provided. In the present disclosure, through obtaining the void fraction of the inside of the heat conduction member, a use limit of the heat conduction member can be identified. Accordingly, the heat conduction member can be operated under a safe heat flux, and a dryout condition can be prevented from occurring in the heat conduction member.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
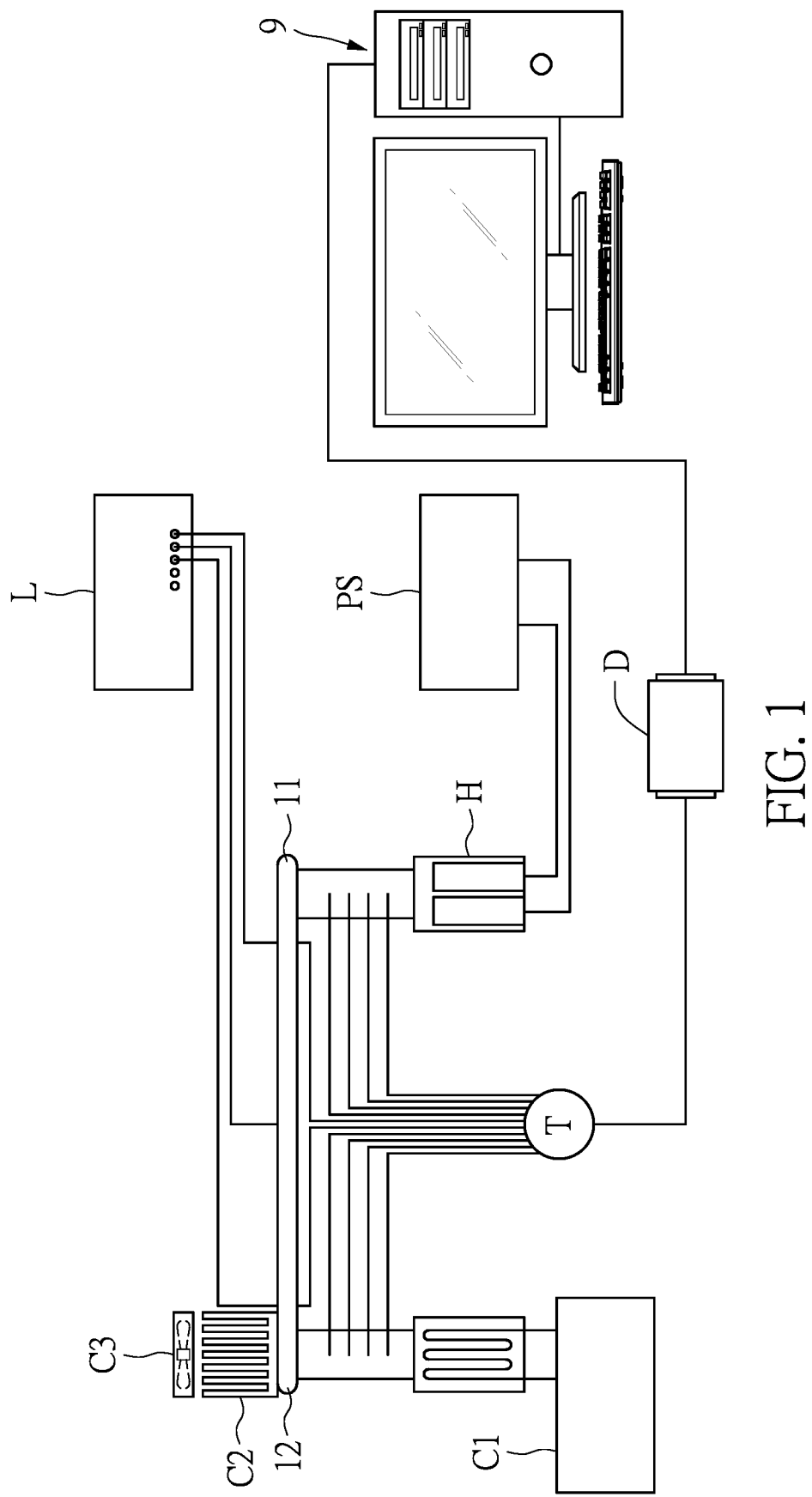
FIG. 1 is a schematic view of a system for measuring a void fraction of an inside of a heat pipe according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Referring to FIG. 1, FIG. 2, FIG. 6, and FIG. 7, a heat conduction member V1 in a first embodiment of the present disclosure is exemplified as being a heat pipe, and FIG. 1 is a schematic view of a system for measuring a void fraction of an inside of a heat pipe. The system is used to measure the heat pipe, and the heat pipe includes a housing 10 and a working fluid wf. In the present embodiment, the system includes a heating device H, a cooling device C1, multiple pairs of electrode pads (P11, P12, P13), and an LCR meter L. The heating device H is configured as a heat source to heat an evaporation end 11 of the heat conduction member V1. The heating device H of the present embodiment can be provided by a power supplier PS.

As shown in FIG. 1, the cooling device C1 is configured for cooling a condensation end 12 of the heat conduction member V1. In addition, in the present embodiment, a heat dissipation device C2 and a heat dissipation fan C3 can be further provided. The heat dissipation device C2 abuts against the condensation end 12 of the heat conduction member V1, and the heat dissipation fan C3 can further dissipate heat from the heat dissipation device C2. Due to different heating powers and the heat dissipation fan C3, a surface temperature of the condensation end, a thermally insulated end, and the evaporation end of the heat pipe (V1) changes with time.

Figure 2:
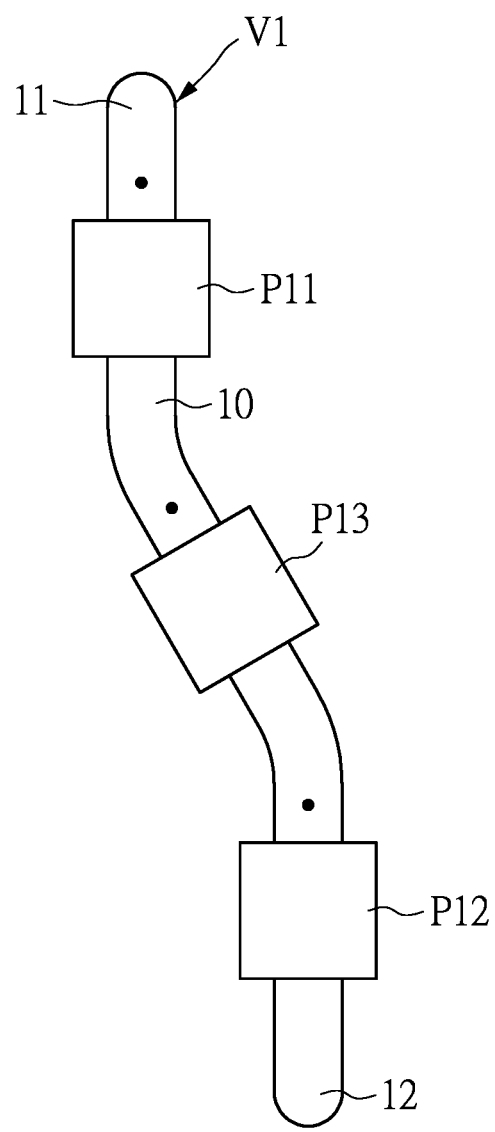
FIG. 2 is a schematic view of the heat pipe and electrode pads according to the present disclosure.

As shown in FIG. 2, the multiple pairs of the electrode pads (P11, P12, P13) of the present embodiment are attached to two opposite surfaces of the heat conduction member V1, respectively. Specifically, the heat conduction member V1 is an elongated heat pipe. A quantity of the electrode pads is at least three pairs, and the at least three pairs are separate from one another. The first pair P11 of the electrode pads are adjacent to the evaporation end 11 of the heat conduction member V1, the second pair P12 of the electrode pads are adjacent to the condensation end 12 of the heat conduction member V1, and the third pair P13 of the electrode pads are adjacent to the thermally insulated end of the heat conduction member V1.

The LCR meter L is electrically connected to electrodes of the electrode pads (P11, P12, P13), so as to measure impedances of the heat conduction member V1.

Referring to FIG. 1, the system of the present embodiment further includes a plurality of thermocouples (as shown by multiple circuit lines of a symbol T), which are used to measure a temperature of the surfaces of the heat conduction member V1, to detect a temperature difference between a heat source point and an outer periphery thereof, and to obtain an input heat flux by measuring the heating device H. The thermocouples (T) are electrically connected to a data acquisition card D, and the data acquisition card D is electrically connected to a computer 9, so as to record the measure temperature.

In the present disclosure, each of the impedances is converted into the void fraction that corresponds to a measured position of the heat conduction member, so as to identify a use limit of the heat conduction member. Accordingly, the heat conduction member can be operated under a safe heat flux, and a dryout condition can be prevented from occurring in the heat conduction member. The conversion of the impedance and the void fraction will be described in greater detail below.

Second Embodiment

Figure 3:
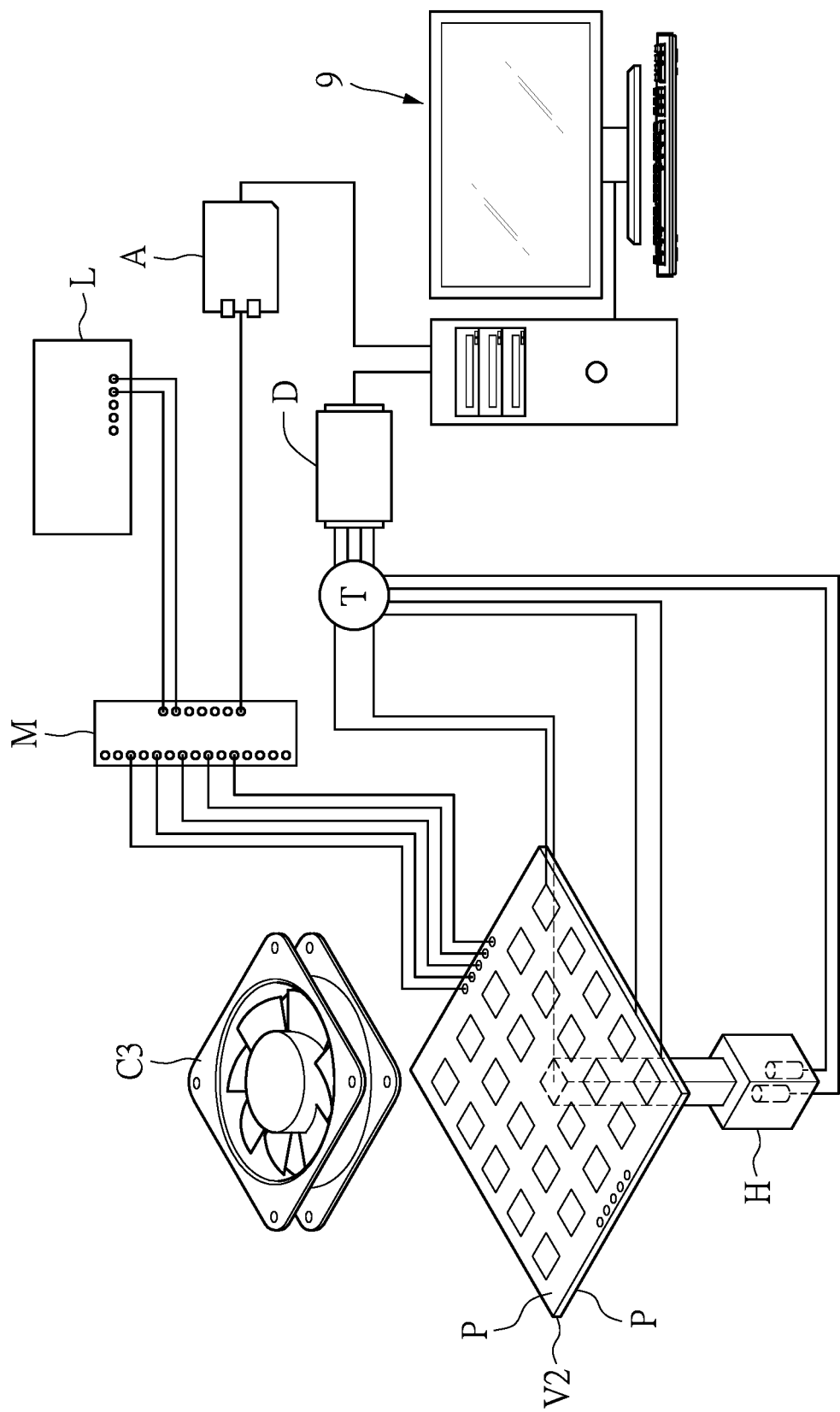
FIG. 3 is a schematic view of a system for measuring a void fraction of an inside of a vapor chamber according to the present disclosure.
Figure 4:
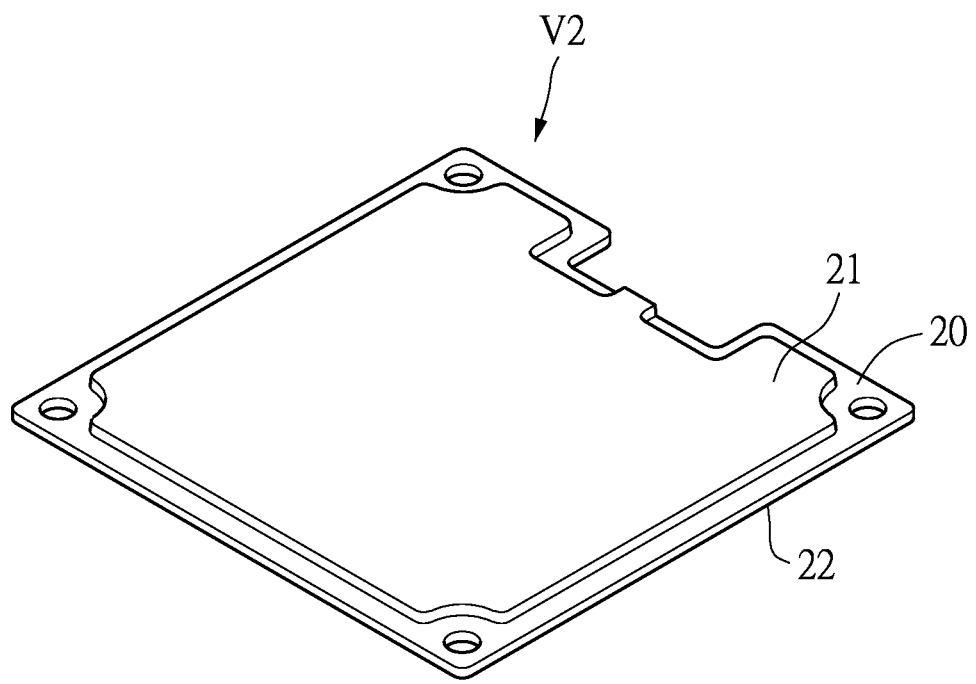
FIG. 4 is a perspective view of the vapor chamber according to the present disclosure.
Figure 5:
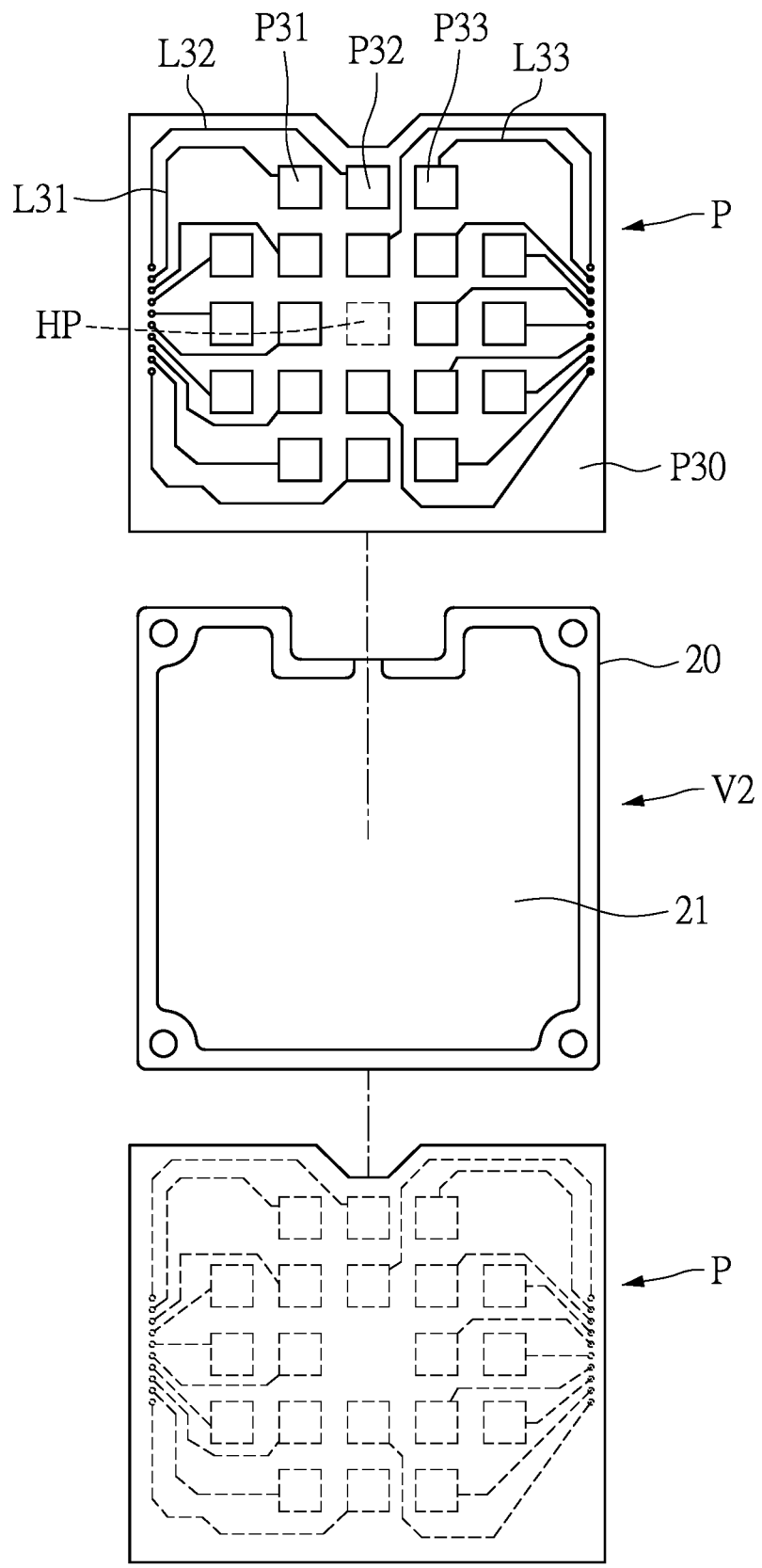
FIG. 5 is a schematic view of the vapor chamber and the electrode pads according to the present disclosure.
Figure 6:
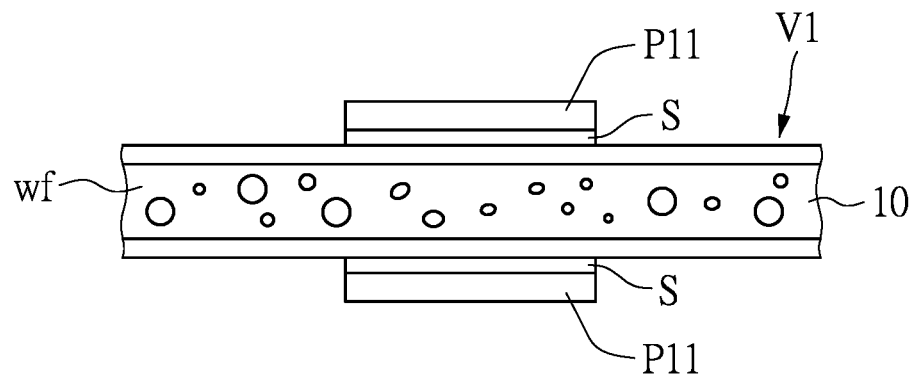
FIG. 6 is a sectional view showing the heat pipe being attached with the electrode pads according to the present disclosure.
Figure 7:
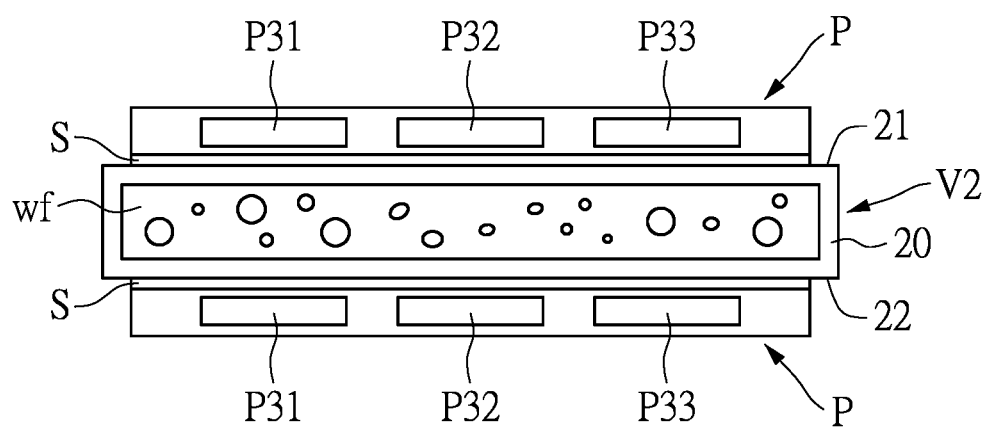
FIG. 7 is a sectional view showing the vapor chamber being attached with the electrode pads according to the present disclosure.

Referring to FIG. 3, FIG. 4, FIG. 5, and FIG. 7, a heat conduction member V2 in a second embodiment of the present disclosure is exemplified as being a vapor chamber, and FIG. 3 is a schematic view of a system for measuring a void fraction of an inside of a vapor chamber. The vapor chamber includes a housing 20, a top surface 21, and a bottom surface 22. Since the vapor chamber has a large area, a pair of electrode pads P are respectively attached to the top surface 21 and the bottom surface 22 of the vapor chamber in the present embodiment. The electrode pads P have a shape similar to that of the vapor chamber, and can be a flexible printed circuit board. Each of the electrode pads P has an insulation substrate P30, and has a plurality of electrodes (P31, P32, P33) and a plurality of conductive wires (L31, L32, L33) arranged on a surface of the insulation substrate P30. The conductive wires (L31, L32, L33) are respectively and electrically connected to the electrodes (P31, P32, P33). Terminal ends of the conductive wires (L31, L32, L33) are arranged at peripheries of the electrode pads P. The insulation substrate P30 can be a polyimide film. The electrode pads P are adhered to the vapor chamber by a double-sided adhesive S that is heat resistant. A hole HP is formed in advance at a center of the electrode pads P (as shown in FIG. 5), so as to reserve space for the heating device H (shown at a lower portion of FIG. 3) to be placed at a center position of the heat conduction member V2 (the vapor chamber). Further, the heat dissipation fan C3 is placed above the vapor chamber for cooling the surface of the vapor chamber.

Referring to FIG. 3, the system of the present embodiment further includes a multiplexer M. The multiplexer M is electrically connected between the electrode pads P and the LCR meter L.

The system of the present embodiment further includes an electronic control board A. The multiplexer M is configured to switch among different channels, and the electronic control board A respectively acquires a measured impedance value of each of the electrodes (P31, P32, P33) of the electrode pads P. For example, in the present embodiment, the electronic control board A can be a microcontroller board (ARDUINO UNO) that is based on the ATmega328P and used in cooperation with ARDUINO control software. However, the present disclosure is not limited thereto. The electronic control board A is electrically connected to the computer 9, and records the measured impedance value by the control software. A capacitive reactance value can be obtained through an impedance formula. Through connection with the data acquisition card D, voltage signals of the thermocouples can be recorded.

Figure 8:
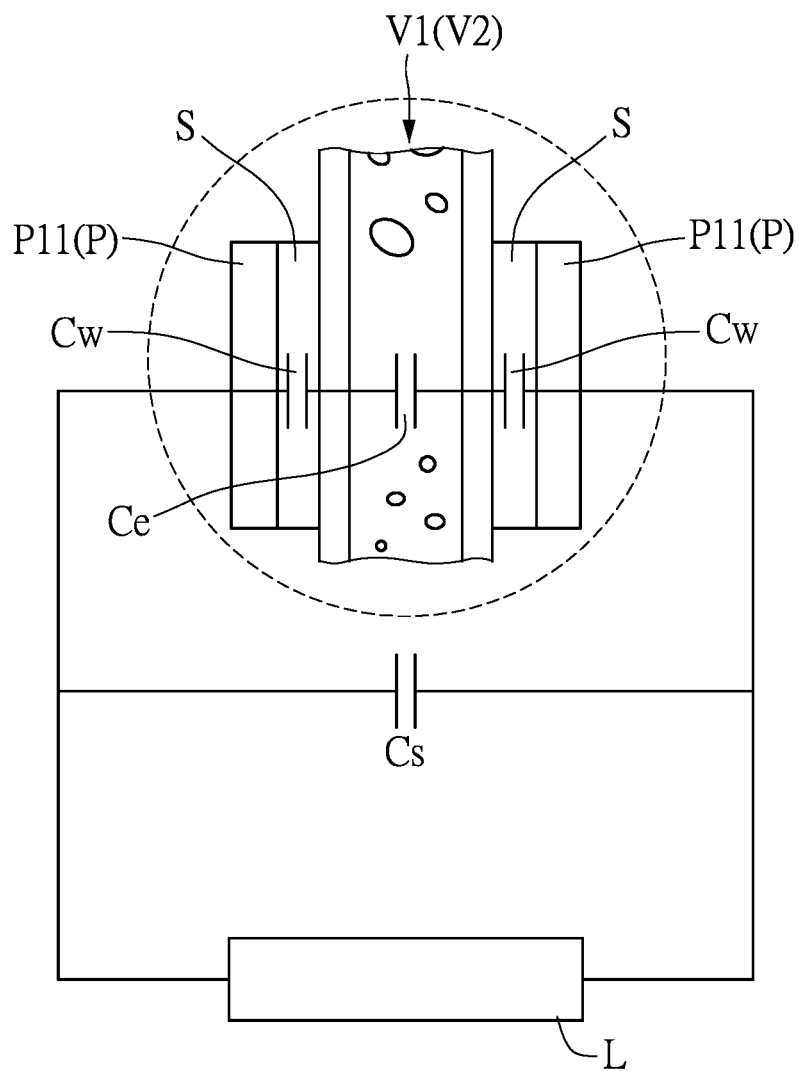
FIG. 8 is an equivalent circuit diagram of a system for measuring a void fraction of an inside of a heat conduction member according to the present disclosure.

As shown in FIG. 8, in the present embodiment, the measured impedance value is used to correspondingly calculate whether the void fraction of the inside of the heat conduction member V1 has exceeded a critical value, so as to timely detect the heat flux that the heat conduction member V1 can bear. The following description reveals how a void fraction of the working fluid inside the heat conduction member can affect the impedance value. In addition, through an analysis of an equivalent circuit shown in FIG. 8, a relation between the void fraction of the inside of the heat conduction member and a capacitance value can be obtained.

Relation of Heat Pipe (V1)

Firstly, the capacitance value is defined as a ratio between an electric charge quantity Q of two ends of the electrode and an electric potential difference Ve of the two ends of the electrode, which can be shown by the following equation (2.1).

$$C = Q/Ve = \varepsilon(A/d) \quad (2.1)$$

Here, $\varepsilon$ is a permittivity, A is an electrode area, and d is a distance between the two electrodes.

Further, any changes in a ratio between liquid and vapor in the heat conduction member will be reflected on the capacitance value. Due to this characteristic, the void fraction of the inside of the heat conduction member can be obtained. The void fraction is defined by the following equation (2.2).

$$\alpha = Vv/(Vv + V_L) \quad (2.2)$$

Here, Vv is a volume of water vapor inside the heat conduction member, and $V_L$ is a volume of liquid water inside the heat conduction member.

Referring to FIG. 8, an equivalent circuit diagram of the heat conduction member of the present embodiment is shown. Here, Cw is a capacitance value between the electrodes and the surfaces of the heat conduction member (V1, V2), Ce is a capacitance value of the working fluid inside the heat conduction member (V1, V2), and Cs is a stray capacitance of a circuit. In the equivalent circuit, 2 Cw and Ce are connected in series with each other, and are then connected in parallel with Cs. A capacitance value Cm measured by the LCR meter L can be defined by the following equation (2.3).

$$Cm = [(Ce\ Cw)/(2Ce + Cw)] + Cs \quad (2.3)$$

From the equation (2.1), Ce can be defined by the following equation (2.4).

$$Ce = \varepsilon_0 \varepsilon_e (A/d) \quad (2.4)$$

Here, $\varepsilon_0$ is a vacuum permittivity ($\varepsilon_0 = 8.85 \times 10^{-12}$ F m$^{-1}$), A is an electrode area, and d is a distance between the two electrodes. Further, $\varepsilon_e$ is an equivalent relative permittivity of the fluid inside the heat conduction member (V1, V2). Since the fluid includes the liquid water and the water vapor, $\varepsilon_e$ can be defined by the following equation (2.5).

$$\varepsilon_e = \alpha \varepsilon_V + (1-\alpha)\varepsilon_L \quad (2.5)$$

Here, $\varepsilon_v$ is a relative permittivity of the water vapor, $\varepsilon_L$ is a relative permittivity of the liquid water, and $\alpha$ is a void fraction of the inside of the heat conduction member. A relation between the void fraction $\alpha$ of the heat conduction member (V1, V2) and the capacitance value (C measured) measured by the LCR meter L can be derived from the above-mentioned equations, as shown by the following equation (2.6).

$$\alpha = \{[(Cw\ d(Cm-Cs)]/[\varepsilon_0 A(2Cs + Cw - 2Cm)] - \varepsilon_L\}/(\varepsilon_v - \varepsilon_L) \quad (2.6)$$

Here, Cw is a capacitance value between the electrode pads and the surfaces of the heat conduction member, Ce is a capacitance value of the working fluid inside the heat conduction member, Cs is a stray capacitance of a circuit, $\varepsilon_v$ and $\varepsilon_L$ are functions of temperature and pressure, A is an electrode area, and d is a distance between one pair of the electrode pads. However, since an effect of the pressure on $\varepsilon_v$ and $\varepsilon_L$ is negligible, $\varepsilon_v$ and $\varepsilon_L$ are taken as the functions of the temperature.

Furthermore, since an overall volume inside the heat pipe is unchanged, and only two fluids (water and water vapor) are present inside the heat pipe, the equation (2.2) can be rewritten into:

$$\alpha = Vv/(Vv + V_L) = 1 - (V_L/(Vv + V_L)) = 1 - (m_L - m_0) \quad (2.7)$$

Here, $m_L$ is a weight of liquid water inside the heat pipe. When the void fraction of the inside of the heat pipe is 0 (e.g., fully filled with the water), $m_0$ is a weight of the liquid water (i.e., $m_L$ at a void fraction of 0).

In the present embodiment, by taking the heat pipe as an example, various samples of the heat pipe (with different void fractions) are used for measuring a weight of the liquid. Then, impedance values of these heat pipes with different void fractions are measured. The void fraction $\alpha$ and the capacitance value Cm are substituted into the equation (2.6). A least square method is further used to perform curve fitting, so as to obtain values of Cw and Cs. Accordingly, a calibration curve of the void fraction $\alpha$ of the inside of the heat pipe can be calculated from the capacitance value Cm.

When taking into consideration that Cw and Cs may change with the temperature (T), in the present embodiment, the above-mentioned steps can be repeated under temperature conditions of 27° C., 50° C., 70° C., and 90° C., so as to obtain the respective relations of the void fraction $\alpha$ under different temperatures.

If a temperature value is in-between curves of two of the above-mentioned temperatures (e.g., 27° C. and 50° C., 50° C. and 70° C., or 70° C. and 90° C.), the void fraction $\alpha$ (Cm, T) can be calculated by using an interpolation method.

Relation of Vapor Chamber (V2)

From the equation (2.1), Cw can be defined by the following equation (2.14):

$$Cw = \varepsilon_0 \varepsilon_W (A/d) \quad (2.14)$$

Here, $\varepsilon_0$ is a vacuum permittivity ($\varepsilon_0 = 8.85 \times 10^{-12}$ F m$^{-1}$), A is an electrode area, and d is a distance between the electrodes and the vapor chamber, and $\varepsilon_w$ is a relative permittivity of a combination of the polyimide film and the double-sided adhesive (e.g., a heat resistant adhesive) on the electrode pads P (e.g., a flexible printed circuit board).

In the present embodiment, a measured capacitance value C', the electrode area A, and a distance d' between the two electrodes are used to obtain the following equation (2.15):

$$\varepsilon_w = (d'C')/A\varepsilon_0 \quad (2.15)$$

In the present embodiment, considering that $\varepsilon_w$ may change with the temperature, $\varepsilon_w$ and Cw under different temperatures need to be calculated first.

Cs is a stray capacitance of a circuit. In an experiment of the vapor chamber, the stray capacitance includes a capacitance of a combination of the multiplexer and the conductive wires connected thereto. In the equivalent circuit, Cs, Ce, and Cw are connected in parallel with each other. The capacitance value is: $(1/(1/Ce+1/Cw))+Cs$.

An average capacitance value of the vapor chamber is measured through the multiplexer, and another average capacitance value of the vapor chamber is directly measured without the multiplexer or any other component. The two average capacitance values are subtracted from each other to obtain the stray capacitance Cs.

From the equations (2.4) and (2.5), it can be known that Ce is a function of relative permittivities of the void fraction $\alpha$, the liquid water, and the water vapor. The relative permittivities $\varepsilon_L$ and $\varepsilon_v$ of the liquid water and the water vapor change with the temperature. For example, in the present embodiment, the LCR meter is used to directly measure a capacitance value C* of the vapor chamber whose void fraction is 0 under the temperatures of 27° C., 50° C., 70° C., and 90° C. The capacitance value C* is defined by the following equation (2.16):

$$C^* = 1/(1/Ce+1/Cw) \quad (2.16)$$

The permittivities $\varepsilon_L$ and $\varepsilon_v$ under different temperatures are substituted into the equations (2.4) and (2.5), so as to obtain Ce values under the different temperatures.

By substituting the above-mentioned Cw, Cs, and Ce into the equation (2.6), a relation of the void fraction and the capacitance value under different temperatures can be obtained.

If a temperature value is in-between curves of two of the above-mentioned temperatures (e.g., 27° C. and 50° C., 50° C. and 70° C., or 70° C. and 90° C.), the void fraction $\alpha$ (Cm, T) can be calculated by using the interpolation method. Moreover, in the present embodiment, data from an uncertainty analysis can also be taken into consideration during experimentation. The uncertainty analysis includes uncertainty in a surface temperature of the heat pipe and the vapor chamber, uncertainty in thermal conductivity of a top portion of a heating block that is in a steady state, uncertainty in capacitance measurement, uncertainty in the void fraction of the heat pipe, and uncertainty in the void fraction of the vapor chamber. The above can be calculated and obtained through the experimental process of the related art.

The present embodiment further includes a method for measuring the void fraction of the inside of the heat conduction member. The method includes the following steps:

heating the evaporation end of the heat conduction member (V1, V2); cooling the condensation end of the heat conduction member (V1, V2); using at least one pair of the electrode pads for measurement of the impedances of the heat conduction member (V1, V2); and establishing a relation between the impedance value measured by the LCR meter and the void fraction of the heat conduction member, so as to obtain the void fraction of the measured position of the heat conduction member.

Details that have been previously mentioned above will not be reiterated hereinafter. In the present embodiment, the calibration curve of the void fraction under different temperatures can be respectively produced according to the results described above. Different heat fluxes and different-sized heat dissipation fans can be incorporated for a temperature curve of each cross section of the heat conduction member at different times. Different heat fluxes and different-sized heat dissipation fans can be incorporated for a capacitance curve of each cross section of the heat conduction member at different times. Different heat fluxes can also be incorporated for void fraction curves of the evaporation end, the condensation end, and the thermally insulated end of the heat conduction member at different times, and these void fraction curves can be drawn on the same graph. In this way, the void fraction of the inside of the heat conduction member can be obtained and visualized.

Beneficial Effects of the Embodiments

In conclusion, in the system and the method for measuring the void fraction of the inside of the heat conduction member provided by the present disclosure, a vapor-liquid distribution in the heat conduction member can be calculated by measuring the capacitance thereof, and a conventional invasive measurement can be avoided. Since the liquid water and the water vapor have different permittivities, and since the permittivity is an important parameter affecting an impedance value, the void fraction of the inside of the heat conduction member can be obtained by measuring the impedance value of the heat conduction member, so that a visualization effect can be provided. In the present disclosure, through obtaining the void fraction of the inside of the heat conduction member, a use limit of the heat conduction member can be identified. Accordingly, the heat conduction member can be operated under a safe heat flux, and a dryout condition can be prevented from occurring in the heat conduction member.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated.

Alternative embodiments will become apparent to those skilled in the art to which the present disclosure pertains without departing from its spirit and scope.

What is claimed is:

1. A system for measuring a void fraction of an inside of a heat conduction member, the system comprising:
    a heating device configured as a heat source to heat an evaporation end of the heat conduction member;
    a cooling device configured for cooling a condensation end of the heat conduction member;
    at least one pair of electrode pads respectively attached to two opposite surfaces of the heat conduction member; and
    an LCR meter electrically connected to the at least one pair of the electrode pads for measuring impedances of the heat conduction member, wherein each of the impedances is converted into the void fraction that corresponds to a measured position of the heat conduction member;
    wherein a relation between the void fraction of the heat conduction member and capacitance values measured by the LCR meter is: $\alpha = \{[(Cw\,d(Cm-Cs)]/[\varepsilon_0\,A\,(2Cs+Cw-2Cm)]-\varepsilon_L\}/(\varepsilon_v-\varepsilon_L)$; wherein $\alpha$ is the void fraction of the heat conduction member, Cm is the capacitance value measured by the LCR meter, Cw is the capacitance value between the electrode pads and the surfaces of the heat conduction member, Ce is the capacitance value of a working fluid inside the heat conduction member, Cs is a stray capacitance of a circuit, $\varepsilon_0$ is a vacuum permittivity, $\varepsilon_v$ is a relative permittivity of water vapor, $\varepsilon_L$ is a relative permittivity of liquid water, $\varepsilon_v$ and $\varepsilon_L$ are functions of temperature and pressure, A is an electrode area, and d is a distance between one pair of the electrode pads; wherein, since the pressure has a negligible effect on $\varepsilon_v$ and $\varepsilon_L$, $\varepsilon_v$ and $\varepsilon_L$ are taken as the functions of the temperature.

2. The system according to claim 1, further comprising a plurality of thermocouples used to measure a temperature of the surfaces of the heat conduction member, to detect a temperature difference between a heat source point and an outer periphery thereof, and to obtain an input heat flux by measuring the heating device.

3. The system according to claim 2, wherein the thermocouples are electrically connected to a data acquisition card, and the data acquisition card is electrically connected to a computer, so as to record the measured temperature.

4. The system according to claim 1, wherein the heat conduction member is a heat pipe, a quantity of the electrode pads is at least three pairs, and the at least three pairs are separate from one another; wherein a first pair of the electrode pads are adjacent to the evaporation end of the heat conduction member, a second pair of the electrode pads are adjacent to the condensation end of the heat conduction member, and a third pair of the electrode pads are adjacent to a thermally insulated end of the heat conduction member.

5. The system according to claim 1, wherein the heat conduction member is a vapor chamber, and an area of the electrode pads is substantially the same as an area of the vapor chamber; wherein a plurality of electrodes and a plurality of conductive wires are arranged on each of the electrode pads, the plurality of conductive wires are respectively and electrically connected to the plurality of electrodes, and terminal ends of the plurality of conductive wires are arranged at peripheries of the electrode pads.

6. The system according to claim 5, further comprising a multiplexer, wherein the multiplexer is electrically connected between the electrode pads and the LCR meter.

7. The system according to claim 6, further comprising an electronic control board, wherein the electronic control board switches the multiplexer to different channels for respectively acquiring a measured impedance value of the electrode pads, and the electronic control board is electrically connected to a computer, so as to record the measured impedance value.

8. A method for measuring a void fraction of an inside of a heat conduction member, comprising steps as follows:
    heating an evaporation end of the heat conduction member;
    cooling a condensation end of the heat conduction member;
    using at least one pair of electrode pads for measurement of impedances of the heat conduction member; and
    establishing a relation between an impedance value measured by an LCR meter and the void fraction of the heat conduction member, so as to obtain the void fraction of a measured position of the heat conduction member;
    wherein the relation between the void fraction of the heat conduction member and capacitance values measured by the LCR meter is: $\alpha = \{[(Cw\,d(Cm-Cs)]/[\varepsilon_0\,A\,(2Cs+Cw-2Cm)]-\varepsilon_L\}/(\varepsilon_v-\varepsilon_L)$; wherein $\alpha$ is the void fraction of the heat conduction member, Cm is the capacitance value measured by the LCR meter, Cw is the capacitance value between the electrode pads and the surfaces of the heat conduction member, Ce is the capacitance value of a working fluid inside the heat conduction member, Cs is a stray capacitance of a circuit, $\varepsilon_0$ is a vacuum permittivity, $\varepsilon_v$ is a relative permittivity of water vapor, $\varepsilon_L$ is a relative permittivity of liquid water, $\varepsilon_v$ and $\varepsilon_L$ are functions of temperature and pressure, A is an electrode area, and d is a distance between one pair of the electrode pads; wherein, since the pressure has a negligible effect on $\varepsilon_v$ and $\varepsilon_L$, $\varepsilon_v$ and $\varepsilon_L$ are taken as the functions of the temperature.

9. The method according to claim 8, further comprising: providing a plurality of thermocouples, so as to measure a temperature of surfaces of the heat conduction member, to detect a temperature difference between a heat source point and an outer periphery thereof, and to obtain an input heat flux by measuring a heating device.

10. The method according to claim 9, further comprising: providing a data acquisition card, wherein the thermocouples are electrically connected to the data acquisition card, and the data acquisition card is electrically connected to a computer, so as to record the measured temperature.

11. The method according to claim 10, wherein the method includes measurement of the impedance value of the heat conduction member that is adjacent to the evaporation end, measurement of the impedance value of the heat conduction member that is adjacent to the condensation end, and measurement of the impedance value of the heat conduction member that is adjacent to a thermally insulated end.

12. The method according to claim 8, wherein the heat conduction member is a vapor chamber, and each of the electrode pads has a shape similar to a shape of the vapor chamber; wherein a plurality of electrodes and a plurality of conductive wires are arranged on each of the electrode pads, the plurality of conductive wires are respectively and electrically connected to the plurality of electrodes, and terminal ends of the plurality of conductive wires are arranged at peripheries of the electrode pads.

13. The method according to claim 12, further comprising: providing a multiplexer, wherein the multiplexer is electrically connected between the electrode pads and the LCR meter.

14. The method according to claim 13, further comprising: providing an electronic control board, wherein the multiplexer is configured to switch among different channels, the electronic control board respectively acquires the measured impedance value of the electrode pads, and the electronic control board is electrically connected to a computer, so as to record the measured impedance value.

\* \* \* \* \*